United States Patent [19]

Papalos

[11] 4,110,367

[45] Aug. 29, 1978

[54] SULFONATED ALKYLPHENOXY ACETONES

[75] Inventor: John George Papalos, Ledgewood, N.J.

[73] Assignee: Diamond Shamrock Corporation, Cleveland, Ohio

[21] Appl. No.: 654,068

[22] Filed: Feb. 2, 1976

[51] Int. Cl.² .................. C07C 143/24; D06P 5/04
[52] U.S. Cl. .................. 260/511; 260/501.19; 260/501.21; 8/169
[58] Field of Search ............... 260/511, 501.19, 501.21

[56] References Cited

U.S. PATENT DOCUMENTS

| | | | |
|---|---|---|---|
| 2,178,829 | 11/1939 | Bruson et al. | 260/512 R |
| 3,766,254 | 10/1973 | Sharman et al. | 260/501.19 |
| 3,809,717 | 5/1974 | Daeuble et al. | 260/512 R |

Primary Examiner—Nicky Chan
Attorney, Agent, or Firm—Theodore J. Dettling

[57] ABSTRACT

The novel compounds, sulfonated alkylphenoxy acetones. In dyeing nylon textiles, with acid dyes, barre' is reduced by using these novel compounds as a dye leveler.

5 Claims, No Drawings

SULFONATED ALKYLPHENOXY ACETONES

BACKGROUND OF THE INVENTION

This invention relates to sulfonated alkylphenoxy acetones, and to the use of these compounds as dye levelers in dyeing synthetic polyamide textiles with acid dyes to alleviate barre'.

In dyeing synthetic polyamide textiles such as fibers, fabrics, or garments (hereafter collectively called "nylons" or "nylon textiles") with acid dyes, there often is obtained barre' or streakiness in the dyed textile due to inherent physical and/or chemical differences existing in the yarns from which the textile has been made. For further information about the causes and manifestations of barre' reference is made to U.S. Pat. No. 3,619,122 and *American Dyestuff Reporter*, Feb. 12, 1968, pgs. 42-47.

To prevent or minimize barre' to an acceptable degree, a variety of anionic surfactants have been employed as dye levelers in the dyeing of nylon textiles with acid dyes. One of the earliest class of anionic surfactants used were the mixed fatty alcohol sodium sulfates. Subsequently, alkyl sulfonate and alkyldiaryl sulfonate surfactants were recommended. More recently, more complex anionics have been alleged to prevent barre', for example: sulfonated sulphones derived from a variety of hydroxy-substituted aryl compounds in U.S. Pat. No. 3,536,438, dialkyl sulfosuccinates in U.S. Pat. No. 3,619,122, alkane-or alkene-amido-benzene-sulphonics in U.S. Pat. No. 3,713,768, and monosulfonated alkylphenoxy glycerol in U.S. Pat. No. 3,809,717. Also, alkyl-substituted diphenyl ether sulfonates, believed to have the general formula shown in U.S. Pat. No. 3,127,441, have been used.

In spite of the abundance of work done to identify anionic surfactants capable of minimizing or preventing barre', a need still exists for new dye levelers considering the great number of different acid dyes employed, the fact that they are typically used in combinations, and the variety of nylon textiles being dyed. In many instances less-than-satisfactory barre' effects are tolerated because a dye leveler suitable from both an economic and a performance standpoint is unavailable.

SUMMARY OF THE INVENTION

Considering this state of the art, it is an object of the present invention to provide new anoinic surfactants that function as dye levelers and are effective in minimizing or preventing barre' effects when used in the dyeing of a variety of nylon textiles with different acid dyes.

This object and other objects and advantages, which will become apparent from the following description and examples, are provided by the novel sulfonated alkylphenoxy acetones hereinafter described, and by their utilization in dyeing nylon textiles with acid dyes.

DESCRIPTION OF THE PREFERRED EMBODIMENTS

The new sulfonated alkylphenoxy acetones that it has been discovered funtion as dye levelers in dyeing nylons with acid dyes have the general formula:

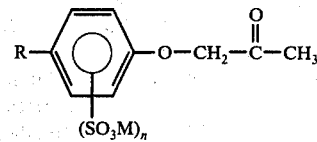

wherein:

R is an alkyl group having an average of 8-20 carbon atoms;

M is hydrogen, sodium, potassium, ammonium, or substituted ammonium; and n is a number of from 1 to 2 inclusive.

The alkyl radical R in the invention compounds may be straight chained or branched, may be saturated or unsaturated, and may be comprised of a mixture of alkyl groups having differing numbers of carbon atoms. Because of its ready availability and low cost, invention compounds produced from dodecyl phenol are preferred.

The substituent M in the invention compounds is hydrogen in the acid form of the compounds, or sodium, potassium, ammonium, or substituted ammonium (by which is meant watersoluble amines such as ethyl amine, dimethyl amine, diethanol amine and the like in the salt form).

Lastly, in the invention compounds n is 1 or 2, or some fractional number between 1 and 2 when the invention compound comprises a mixture of the monosulfonated and disulfonated compounds, for example, 1.5 when equal parts of each are present. Best dye leveling has been obtained when n is 1.

The invention compounds are readily prepared, as illustrated and described in more detail in the following examples, by first sulfonating a phenol having a para-substituted alkyl group having an average 8-20 carbon atoms with enough sulfonating agent (chlorosulfonic acid, oleum and the like) to give the desired average number of sulfonic acid groups. This reaction is well known, as shown for example in U.S. Pat. Nos. 2,249,757 and 3,707,352, and is most easily done in solution using an organic solvent inert to the reaction such as ethylene dichloride, 1,2-dichloropropane and the like. The resulting sulfonated intermediate is neutralized with an aqueous sodium or potassium hydroxide solution, and about a stoichiometric quantity of monochloroacetone added slowly over a period of 30-60 minutes. Additional aqueous sodium or potassium hydroxide is added concurrently with the chloroacetone to neutralize the HCl generated and at a rate that maintains the reaction at a pH of at least 8. The resulting phenoxy ether product, which can be recovered and purified by conventional means, will be in the form of the salt of the alkali metal hydroxide used. The acid form is produced by reacting the salt with a suitable acid, such as HCl, and purifying and isolating by conventional means. When the ammonium or substituted ammonium salt is desired, ammonium hydroxide or a watersoluble amine is used in the synthesis in place of the sodium or potassium hydroxide. Alternatively, the acid form of the invention compound can be reacted with the desired ammonium compound. The synthesis of sulfonated alkylphenoxy compounds by procedures similar to that described herein are disclosed in U.S. Pat. Nos. 2,178,830, 3,707,352 and 3,809,717.

As previously described, the invention compounds have been discovered to be effective dye levelers for nylon textiles dyed with acid dyes, being effective anti-barre' agents for a variety of nylon dye combinations. Generally, the nylon textiles, acid dyes, and dyeing procedures utilized are conventional.

Thus, the nylon textiles to be dyed may be in the form of fibers (either staple or continuous), fabrics (woven, nonwoven, knitted and the like), or finished textile goods; and may consist of only synthetic polyamide, or may consist of blends of the polyamide with other textile materials (such as polyesters, polyacrylonitriles, wool, cotton, and the like) compatible with the dyes and the dyeing conditions used for the nylon.

The acid dyes employed, generally, may be any of those normally used for dyeing nylon, as for example, those belonging to the azo, anthraquinone, quinophthalone, phthalocyanine or triphenylmethane classes of dyes or the nitro of formazane dyestuffs, which optionally may contain complex-bound metals, such as copper, nickel, chromium or cobalt.

The quantity of the invention sulfonated alkylphenoxy acetone employed usually will be the minimum necessary to provide an acceptably uniform and streak-free dyed textile (dye-leveling quantity). Generally, depending on a number of interrelated factors, such as type of nylon, type and quantity of the dye, dyeing conditions and the like, acceptable alleviation of barre' can be achieved with about 0.25 to 4.0 parts by weight of the invention compound per 100 parts by weight of the nylon textile being dyed. In most cases, from about 0.5 to 1.0 part will be optimum from a cost/performance standpoint. Since the invention compound is facilely produced, marketed, and used in industrial dyeing as an aqueous dispersion, the salt, being most soluble, will normally be employed. The acid form of the invention compounds, however, is equally suitable when its lesser solubility does not cause problems. Because of their lower costs, the alkali metal salts are normally preferred for dye leveling. While only one of the invention compounds is usually employed, mixtures of two or more may be used. Further, for some dyeings, other anionic surfactants may advantageously be used in conjunction with the invention compounds.

With respect to the dyeing process, the invention dyeleveler compounds like those of the prior art, normally, are most effective if added to the dye bath containing the nylon textile before the dye, and preconditioning the textile for some finite period, such as 5 to 30 minutes, before dye addition. Dyeing temperatures normally vary between 60° and 120° C., with 80°-100° C. being typical. When the textile is preconditioned, temperatures of about 25°-60° C. are usual, followed by higher temperatures, such as 80°-120° C., after the dye addition. During dyeing, the bath typically is maintained at a pH of about 6 to 8, and is lowered to about 4.0 or less near the end of the cycle if more complete dye exhaust and improved washfastness is desired. Control of pH is usually achieved with compounds such as acetic acid, formic acid, dilute sulfuric or phosphoric acid, ammonium sulfate, sodium acetate and the like. Other materials often used in acid dyeing may also be used with the invention compounds, as for example: nonionic surfactants to improve fabric wetting or control the degree of dye dispersion; organic water-miscible solvents, such as isopropanol, to predisperse the acid dyes or assist in fabric wetting; and chelating agents, such as ethylenediamine tetra-acetic acid, to tie up iron and other polyvalent metal ions that can adversely effect the dyeing process or product quality. After dyeing, the nylon textile is normally washed with water before being dried.

EXAMPLE 1

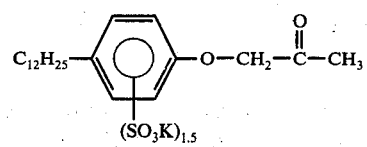

A compound of the above formula is produced as follows: 256 parts (2.2 moles) of chlorosulfonic acid is added over two hours to an agitated solution of 272 parts of p-dodecylphenol (1 mole based on OH number) and 400 parts of ethylene dichloride maintained at 0°-25° C. The resulting mixture is agitated at 10°-25° C. for about six hours under a slight vacuum to remove HCl. Then, 1092 parts of 15% aqueous KOH (2.93 moles) is added with stirring while maintaining the temperature at 30°-50° C. Next, 548 parts of 15% aqueous KOH (1.47 moles) and 92 parts of monochloroacetone acid (1 mole) are concurrently added to the stirred reaction mixture within a 30 minute period while maintaining the temperature at 68°-72° C., care being taken to add the KOH at a rate sufficient to maintain the reaction mixture at a pH of 8 or more (measured on a 5% solution). The reaction mixture is refluxed (70°-75° C.) for six hours with vigorous agitation, cooled, and allowed to stand for 16 hours at 40°-50° C. The reaction mixture divides into two layers and the top aqueous layer is discarded. 800 parts of water are added to the bottom organic layer and its pH adjusted to 9 ± 0.5 using either 10% HCl or 15% KOH. All of the ethylene dichloride is azeotropically distilled off and the batch cooled. Lastly, 200 parts of isopropanol is admixed in and the pH adjusted to 9 ± 0.5. The product is storage stable and usable as a leveling agent in dyeing nylon textiles.

EXAMPLE 2

The sulfonated dodecylphenoxy acetone of Example 1 was evaluated as a dye leveler in a series of dye tests employing an Ahiba laboratory dyeing machine, 10-gram samples of a nylon tiger stripe test fabric, and the following dyestuffs:

| BROWN DYE | |
|---|---|
| 0.8% o.w.f. | Acid Blue #232 |
| 0.25% o.w.f. | Acid Yellow #49 |
| 0.05% o.w.f. | Acid Red #99 |
| 0.05% o.w.f. | Acid Bule #247 |
| BLUE DYE | |
| 0.25% o.w.f. | Acid Blue #122 |
| GREEN DYE | |
| 0.25% o.w.f. | Acid Green #25 |

The dyeing procedure used for each test consisted of: preparing 300 mls of a dyebath containing 2% o.w.f. of ammonium sulfate and either 0.5% or 1.0% o.w.f. of the dye leveler, setting the bath at 120° F., entering the fabric sample and running ten minutes at 120° F., adding the dyestuff and running ten minutes at 120° F., raising the bath temperature about 2°/minute to 212° F. and running for 60 minutes more, adding to 0.5% o.w.f. of acetic acid and running for 30 minutes at 212° F., rinsing the fabric with warm water, spin-extracting the rinse water, and air drying the fabric.

The results of the dye-leveling tests are compiled in the Table. In the tests, the improvement in color uniformity (alleviation of barre') over a blank (no dye leveler) was ascertained independently for each dyestuff. Color uniformity ratings were based on an arbitrary scale of 1-5, with 1 being the poorest and 5 the best. The color uniformity ratings shown in the Table are the average of five ratings by different textile chemists. From this data it can be seen that the invention compound of Example 1 functions as a dye leveler in dyeing a nylon textile with a variety of acid dyes. For some dyes and nylon textiles, better leveling may be achieved with invention compounds having only one sulfonate group.

EXAMPLE 2

Dye Tests

| Dye Color | Example 1 | Blank |
|---|---|---|
| Brown | | |
| 0.5% o.w.f. | 2.8 | 1.0 |
| 1.0% o.w.f. | 3.2 | |
| Blue | | |
| 0.5% o.w.f. | 2.4 | 1.0 |
| 1.0% o.w.f. | 2.9 | |
| Green | | |
| 0.5% o.w.f. | 2.5 | 1.0 |
| 1.0% o.w.f. | 3.4 | |

The invention sulfonated alkylphenoxy acetones may also be employed in other applications where sulfonate-containing surfactants are used. For example, they may be used as detergents, dispersing agents, emulsifying agents for latex polymerizations, textile wetting agents, penetrating agents, leather tanning agents, textile scouring agents, and the like. For some of these applications, the presence of a carbonyl group in the molecule can be advantageous because of its reactivity potential.

What is claimed is:

1. A compound having the formula

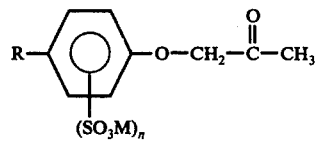

wherein:
R is an alkyl group having 8-20 carbon atoms;
M is hydrogen, sodium, potassium, ammonium, ethyl ammonium, dimethyl ammonium, or diethanol ammonium; and
$n$ is a number of from 1 to 2 inclusive.

2. The compound of claim 1 wherein $n$ is 1.

3. The compound of claim 1 wherein R is an alkyl group having 12 carbon atoms.

4. The comound of claim 3 wherein M is potassium or sodium.

5. The compound of claim 4 wherein $n$ is 1.

* * * * *